(12) United States Patent
Sigmon, Jr.

(10) Patent No.: US 9,314,597 B2
(45) Date of Patent: Apr. 19, 2016

(54) CLIP FOR CATHETER MANAGEMENT (71) Applicant: Cook Medical Technologies LLC, Bloomington, IN (US)

(72) Inventor: John Crowder Sigmon, Jr., Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 72 days.

(21) Appl. No.: 14/109,149

(22) Filed: Dec. 17, 2013

(65) Prior Publication Data

US 2014/0259544 A1 Sep. 18, 2014

Related U.S. Application Data (60) Provisional application No. 61/791,197, filed on Mar. 15, 2013.

(51) Int. Cl.
*A61M 25/02* (2006.01)
*A61M 25/00* (2006.01)
*A61M 25/01* (2006.01)
*A61B 1/00* (2006.01)

(52) U.S. Cl.
CPC ............ *A61M 25/02* (2013.01); *A61B 1/00128* (2013.01); *A61M 25/0097* (2013.01); *A61M 25/01* (2013.01); *A61M 2025/024* (2013.01); *Y10T 24/14* (2015.01); *Y10T 29/49826* (2015.01)

(58) Field of Classification Search
USPC ............ 294/137, 25, 26, 175; D24/135, 143; 600/554, 567; 604/160, 187
See application file for complete search history.

(56) References Cited

U.S. PATENT DOCUMENTS

| 4,209,015 | A | * | 6/1980 | Wicks | 604/165.03 |
| 4,445,893 | A | * | 5/1984 | Bodicky | 604/165.04 |
| D318,733 | S | * | 7/1991 | Wyzgala | D24/112 |
| D320,276 | S | * | 9/1991 | Baum | D24/113 |
| 5,334,157 | A | * | 8/1994 | Klein et al. | 604/160 |
| D352,108 | S | * | 11/1994 | Mohiuddin | D24/112 |
| 5,372,592 | A | * | 12/1994 | Gambale | 604/523 |
| 5,830,183 | A | | 11/1998 | Krieger | |
| 5,954,707 | A | | 9/1999 | Kanesaka et al. | |
| 6,499,781 | B1 | * | 12/2002 | Flynn | 294/159 |
| 7,507,200 | B2 | * | 3/2009 | Okada | 600/104 |

(Continued)

FOREIGN PATENT DOCUMENTS

| DE | 92 12 575 U1 | 11/1992 |
| EP | 1 306 100 A1 | 5/2003 |
| WO | WO 2009/039296 A1 | 3/2009 |

OTHER PUBLICATIONS

International Search Report for corresponding PCT Application No. PCT/US2014/026436, dated Jul. 7, 2014, 7p.

*Primary Examiner* — Paul T Chin
(74) *Attorney, Agent, or Firm* — Brinks Gilson & Lione (57) ABSTRACT

A catheter management clip is provided which provides at least one curved clip on the handle of a device requiring a catheter. The placement of the curved clip on the handle allows the looping of the catheter from either the top opening or bottom opening of the clip and therefore the catheter can be used by both left and right handed users. In one preferred embodiment, a clip is located on either side of the handle and oriented so that the two clips are pointed in the same direction. In another embodiment, two clips are located on the same side of the handle and are connected so that the openings of the two clips are pointing in opposite directions.

16 Claims, 5 Drawing Sheets

(56) References Cited

U.S. PATENT DOCUMENTS

D650,078 S * 12/2011 Efinger et al. ............... D24/140
8,574,244 B2 * 11/2013 Reynolds ..................... 606/144
2001/0049504 A1    12/2001 Gautsche et al.
2004/0201236 A1 * 10/2004 Adelson ....................... 294/159
2007/0035144 A1 *  2/2007 Buzby et al. ................. 294/137
2010/0312227 A1   12/2010 House

* cited by examiner

Figure 7

# CLIP FOR CATHETER MANAGEMENT

RELATED APPLICATION

The present application claims priority to U.S. Provisional Application Ser. No. 61/791,197 filed on Mar. 15, 2013, the contents of which is herein incorporated by reference in its entirety.

BACKGROUND

The present invention generally relates to a catheter management clip. More particularly, the present invention relates to a catheter management clip located on the handle of a device requiring a catheter.

Catheters are tubular medical devices for insertion into the body in order to perform a variety of medical procedures. These catheters can vary in size, shape and function, and often consist of a long, flexible, and thin tubular portion that is connected to an accessory or device that a healthcare professional uses to perform the medical procedure. Catheters are generally very fine and delicate in nature, and should be handled, stored, and shipped with great care.

In addition to the delicate nature of catheters, the sterility of catheters is also of paramount importance so as to prevent infection within the body.

During the course of various medical procedures, a healthcare professional often works with a variety of catheter-requiring devices. As a function of practicality, given the length of these devices (catheters often range from 170-200 cm long) and the speedy nature of these procedures, healthcare professionals must balance maintaining the sterility and organization of these lengthy devices with the need to perform the procedure efficiently. Oftentimes catheters can become tangled or dropped, requiring additional time to either untangle the catheter or the use of a brand new catheter entirely.

Current devices in the prior art generally provide for the organization and management of catheters that do not require constant manipulation. These devices either provide minimal support for the catheter in use, or an additional step must be taken to secure these devices onto the catheter.

BRIEF SUMMARY

One or more embodiments of the present invention provide for an improved catheter management clip that both increases the efficiency of performing the medical procedure while also increasing the ability of healthcare professionals to manage and maintain the sterility of the catheters they are using.

The shape and location of the clip on the handle allows for easy looping of the catheter onto the clip when the catheter is temporarily not in use, allowing for the user to manage the long length of the catheter and to prevent the very real problem of tangled catheters and devices fall off operating tables. Additionally, the easy looping of the catheter onto the clip does not limit the use of the device to either left handed or right handed users. By providing users the ability to easily loop these catheters, the length of the catheter can be managed throughout the procedure.

An added benefit of the device is the easy management and loading of the catheter onto the device from the packaging. As catheters come in a looped packaging, the embodiment of the present invention allows the user to hook the loops directly into the clip, without having to uncoil and recoil the catheter about the clip.

Pictured in the current embodiment is the improved catheter management clip located on the body of a sphincterotome. However, the improved catheter management clip can be attached to the body of any device using a catheter which can span a wide variety of applications—from endoscopy to vascular applications.

In one embodiment of the present invention, the improved catheter management clip is composed of a curved device that is attached to the body of the handle of the device. The clip is situated so that the opening is curved inwards towards the body of the handle.

In a preferred embodiment, two of these catheter management clips are located on either side of the body of the handle so that the openings of the clip are curved in the same direction.

In another preferred embodiment, two of these catheter management clips are both located on the same side of the body of the handle but are attached in a way so that the openings of the clips are curved in opposite directions.

In another preferred embodiment, the catheter management clip is lined with a rubber pad or similar material to provide for added traction so as to reduce any slipping that may occur.

In another preferred embodiment, the catheter management clip is connected to the body of the handle by a hinge.

In another preferred embodiment, the body of the handle has a recess that allows the catheter management clip to be stored in when not in use.

In another preferred embodiment, the catheter management clip can be removed from the body of the handle. The catheter management clip can engage with a portion of the body of the handle. In one embodiment, engagement portion on the body of the handle allows the catheter management clip to slide onto the body of the handle. In another embodiment, the engagement portion on the body of the handle allows the catheter management clip to snap onto the body of the handle.

DETAILED DESCRIPTION OF THE DRAWINGS AND THE PRESENTLY PREFERRED EMBODIMENTS

Figure 1:
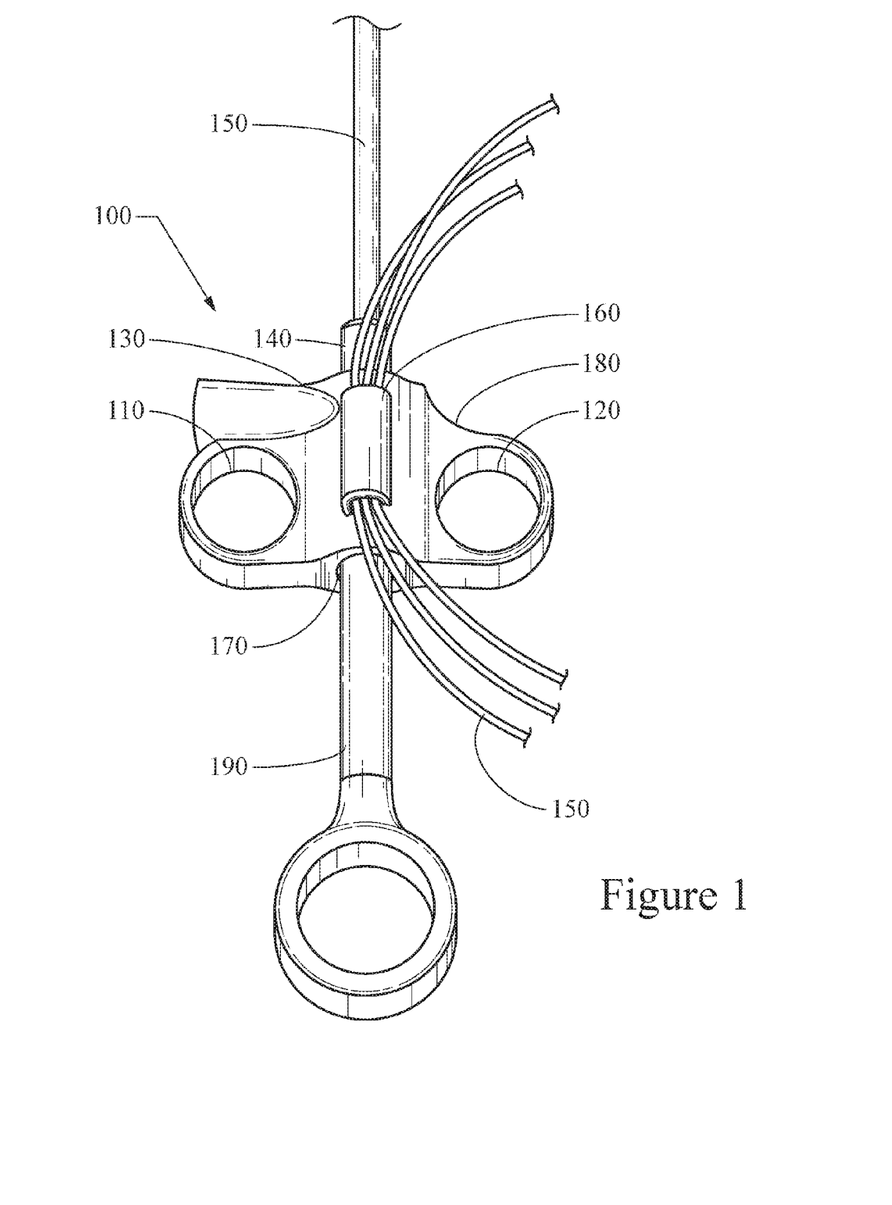
FIG. 1 illustrates a catheter management clip located on a sphincterotome handle according to an embodiment of the present invention.
Figures 4, 5:
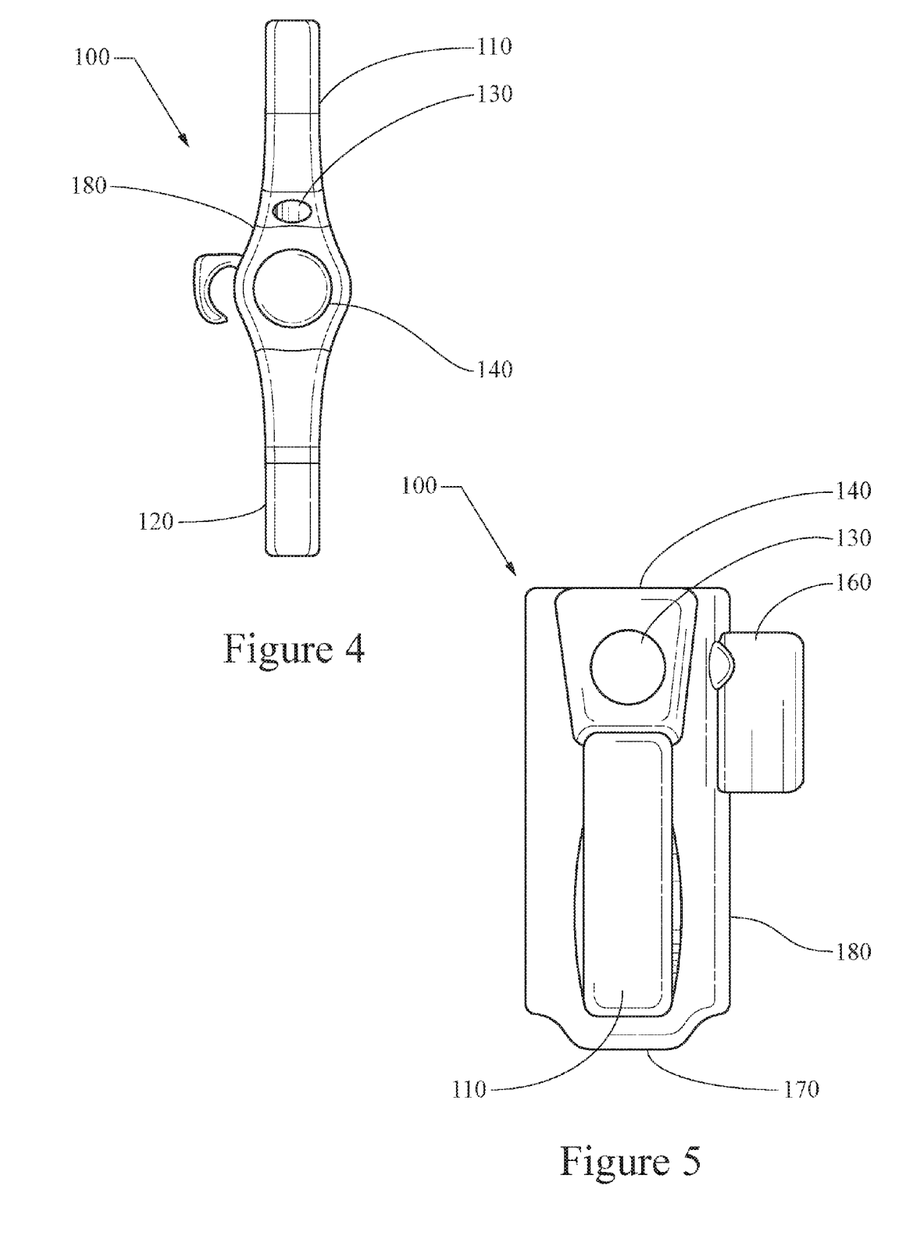
FIG. 4 illustrates a side view of the catheter management clip of FIG. 1.
FIG. 5 illustrates a top view of the catheter management clip of FIG. 1.

FIG. 1, FIG. 4 and FIG. 5 illustrate a one clip catheter management device 100 according to an embodiment of the present invention. In this preferred embodiment, the one clip management device 100 has a catheter management clip 160 that is located on a sphincterotome handle. The one clip catheter management device 100 includes a first user ring 110, a second user ring 120, an electrical power source 130, an opening for a slidably disposed stem 140, a catheter shaft 150, a catheter shaft 155, a catheter management clip 160, a device bottom entrance 170, a handle body 180, and a stem 190.

In the one clip catheter management device 100, the one clip catheter management device 100 is made up of two main parts—the handle body 180 and the catheter management clip 160. The handle body 180 has a first user ring 110 and second user ring 120 on either side of its body which allows a user's finger to hold the handle body 180 steady while using the device. The handle body 180 also provides for an electrical power source 130 which provides a connector for connecting a cutting wire (not shown) to an electrical power source. As well, the handle body 180 has a hollow center that holds the stem 190 so that it rests between the opening for a slidably disposed stem 140 and the device bottom entrance 170. The distal end of the stem 190 is attached to the catheter shaft 155. The catheter shaft 150 is then attached to the distal end of the catheter shaft 155.

In this embodiment, one catheter management clip 160 is located on the center of the handle body 180. The catheter management clip 160 has a curved body that prevents the catheter shaft 150 from escaping once it is looped about the catheter management clip 160.

In using the one clip catheter management device 100, the user can loop the catheter shaft 150 through the single catheter management clip 160 by inserting the coils of the catheter shaft 150 through the single management clip 160. The shape and placement of the catheter management clip 160 allows for convenient looping by both left and right handed users.

In another embodiment, the catheter management clip 160 is attached to the body of an ERCP catheter. In another embodiment, the catheter management clip 160 is attached to any device that can be connected to a catheter shaft 150.

In another embodiment, the catheter management clip 160 is lined with a rubber pad to provide for added traction to prevent the looped catheter shaft 150 from slipping. In another embodiment, the catheter management clip 160 is lined with a silicon pad to provide for added traction to prevent the looped catheter shaft 150 from slipping. In another embodiment, the catheter management clip 160 is lined with any material that increases the friction between the catheter management clip 160 and the catheter shaft 150.

In another embodiment, the gap between the catheter management clip 160 and the side of the handle body 180 is reduced or increased depending on the diameter of the catheter used.

Figure 2:
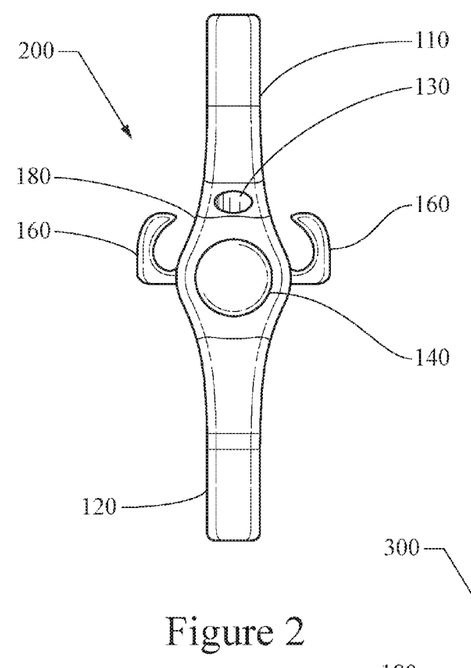
FIG. 2 illustrates a top view of a catheter management clip located on a sphincterotome handle according to another embodiment of the present invention.
Figure 6:
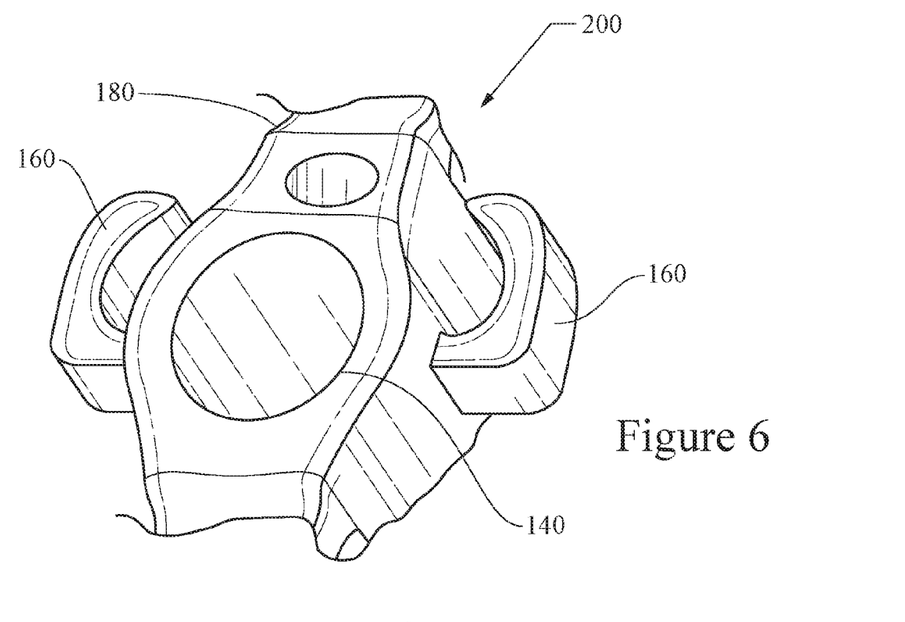
FIG. 6 illustrates an enlarged top view of the catheter management clip of FIG. 2.

FIG. 2 and FIG. 6 illustrate a two lateral clip catheter management device 200 according to an embodiment of the present invention. The two lateral clip catheter management device 200 includes a first user ring 110, a second user ring 120, an electrical power source 130, an opening for a slidably disposed stem 140, two catheter management clips 160, and a handle body 180.

The two lateral clip catheter management device 200 is similar to the one clip catheter management device 100 of FIG. 1. In particular, the two lateral clip catheter management device 200 comprises two main parts—the handle body 180 and two catheter management clips 160. The handle body 180 is configured in the same way as the handle body 180 of FIG. 1. In this embodiment, there are two catheter management clips 160 that are located on opposite sides of the center of the body of the handle body 180. Like the catheter management clip 160 of FIG. 1, both of the catheter management clips 160 have a curved body that prevents the catheter shaft 150 of FIG. 1 from escaping once it is looped about the two catheter management clips 160. In this embodiment, the two catheter management clips 160 are located so that their openings are both curved in the same direction.

In using the two lateral clip catheter management device 200, the user can loop the catheter shaft 150 of FIG. 1 through either one of the catheter management clips 160 by inserting the coils of the catheter shaft 150 of FIG. 1 through either of the catheter management clips 160. The shape and placement of the two catheter management clips 160 not only allows for convenient looping by both left and right handed users, but also an additional place to loop the catheter shaft 150 of FIG. 1 as is convenient for the user.

In another embodiment, the two catheter management clips 160 are placed so that both openings curve in the direction of the opening for a slidably disposed stem 140. In a further embodiment, the two catheter management clips 160 are placed so that both openings curve in the direction of the device bottom entrance 170 of FIG. 1. In a further embodiment, the two catheter management clips 160 are placed on the handle body 180 so that the openings of the catheter management clips 160 are not facing in the same direction.

In another embodiment, the two catheter management clips 160 are attached to the body of an ERCP catheter. In another embodiment, the two catheter management clips 160 are attached to any device that can be connected to a catheter shaft 150.

In another embodiment, the two catheter management clips 160 are lined with a rubber pad to provide for added traction to prevent the looped catheter shaft 150 from slipping. In another embodiment, the two catheter management clips 160 are lined with a silicon pad to provide for added traction to prevent the looped catheter shaft 150 from slipping. In another embodiment, the two catheter management clips 160 are lined with any material that increases the friction between the two catheter management clips 160 and the catheter shaft 150.

In another embodiment, the gap between the two catheter management clips 160 and the side of the handle body 180 is reduced or increased depending on the diameter of the catheter used.

Figure 3:
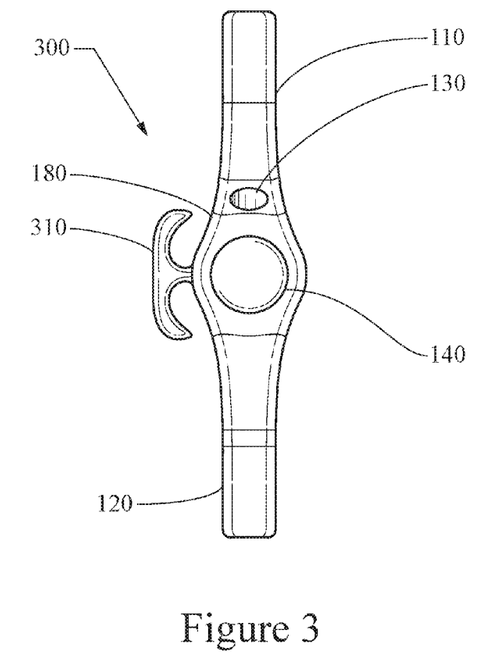
FIG. 3 illustrates a top view of a catheter management clip located on a sphincterotome handle according to another embodiment of the present invention.

FIG. 3 illustrates a two connecting clip catheter management device 300 according to an embodiment of the present invention. In this preferred embodiment, the connected catheter clip 310 of the two connecting clip catheter management device 300 is located on a sphincterotome handle. The two connecting clip catheter management device 300 includes a first user ring 110, a second user ring 120, an electrical power source 130, an opening for a slidably disposed stem 140, a handle body 180, and connected catheter clip 310.

In the two connecting clip catheter management device 300, the two connecting clip catheter management device 300 is, like the one clip catheter management device 100 of FIG. 1, made up of two main parts—the handle body 180 and the connected catheter clip 310. The handle body 180 is configured in the same way as the handle body 180 of FIG. 1. In this embodiment, the connected catheter clip 310 is located on the center of the body of the handle body 180. The connected catheter clip 310 has two curved portions that prevent the catheter shaft 150 of FIG. 1 from escaping once it is looped about the connected catheter clip 310. In this embodiment, the connected catheter clip 310 is located so that the openings are curved towards the ends of the first user ring 110 and the second user ring 120.

In using the two connecting clip catheter management device 300, the user can loop the catheter shaft 150 of FIG. 1 through either side of the connected catheter clip 310 by inserting the coils of the catheter shaft 150 of FIG. 1 through either the proximal or distal openings of the connected catheter clip 310. The shape of the connected catheter clip 310 not only allows for convenient looping by both left and right handed users, but also an additional place to loop the catheter shaft 150 of FIG. 1 as is convenient for the user.

In another embodiment, the connected catheter clip 310 is placed so that the openings of the connected catheter clip 310 curves in the direction of the opening for a slidably disposed stem 140 of FIG. 1 and device bottom entrance 170 of FIG. 1. In a further embodiment, the connected catheter clip 310 is placed at the center of the handle body 180.

In another embodiment, the connected catheter clip 310 is attached to the body of an ERCP catheter. In another embodiment, the connected catheter clip 310 is attached to any device that can be connected to a catheter shaft 150.

In another embodiment, the connected catheter clip 310 is lined with a rubber pad to provide for added traction to prevent the looped catheter shaft 150 from slipping. In another embodiment, the connected catheter clip 310 is lined with a silicon pad to provide for added traction to prevent the looped catheter shaft 150 from slipping. In another embodiment, the connected catheter clip 310 is lined with any material that increases the friction between the connected catheter clip 310 and the catheter shaft 150.

In another embodiment, the gap between connected catheter clip 310 and the side of the handle body 180 is reduced or increased depending on the diameter of the catheter used.

Figure 7:
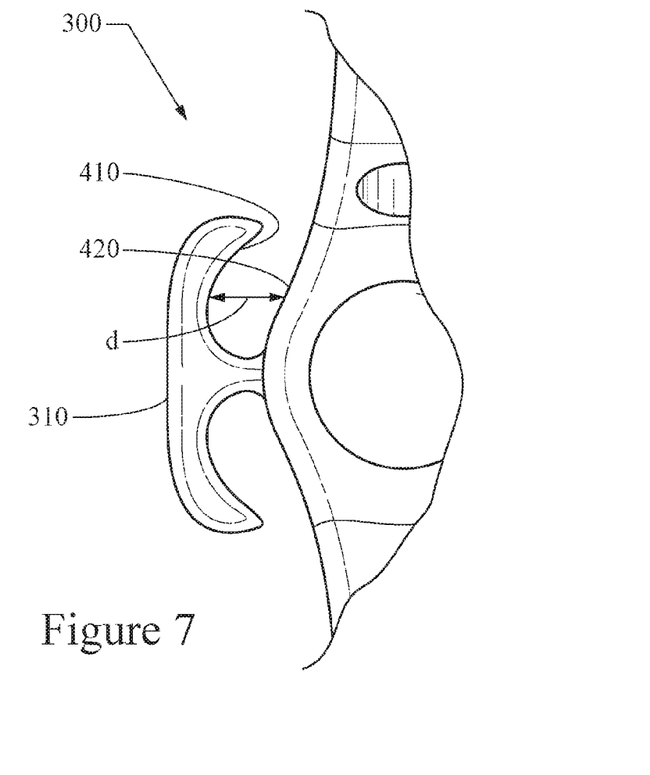
FIG. 7 illustrates an enlarged view of the catheter management clip of FIG. 3.

FIG. 7 illustrates an enlarged view of two connecting clip catheter management device 300 as described in FIG. 3. The two connecting clip catheter management device 300 of FIG. 7 shows a two connecting clip catheter management device 300 of FIG. 3 which includes an interior surface of clip 410, an exterior surface of handle 420, and a distance "d" between the interior surface of clip 410 and exterior surface of handle 420.

In one embodiment, the interior surface of clip 410 curves inwardly to the exterior surface of handle 420 so that the distance "d" between the interior surface of clip 410 and exterior surface of handle 420 decreases across the length of the clip.

In another embodiment, the interior surface of clip 410 remains parallel to the exterior surface of handle 420 so that the distance "d" between the interior surface of clip 410 and exterior surface of handle 420 stays constant across the length of the clip.

The aforementioned description of the relationship of the interior surface of clip 410 and the exterior surface of handle 420 is applicable to all embodiments of the catheter management clip.

In another embodiment, the interior surface of clip 410 is sloped so that the distance "d" between the interior surface of clip 410 and the exterior surface of handle 420 is greater near the opening for a slidably disposed stem 140 than near the device bottom entrance 170. This sloping creates a funnel that better helps to guide the catheter shaft 150 into the connected catheter clip 310.

Figure 8:
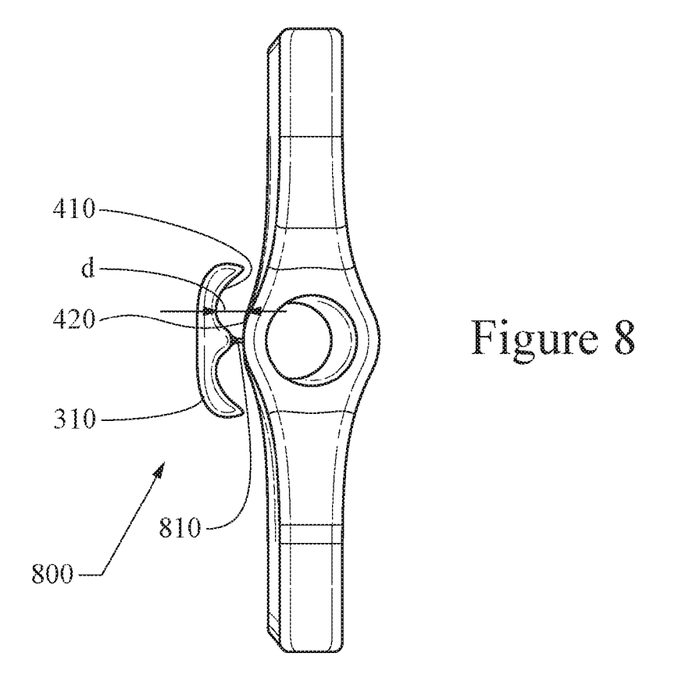
FIG. 8 illustrates a top view of the catheter management clip attached to the body of a handle by a hinge according to an embodiment of the present invention.

FIG. 8 illustrates a movable clip catheter management device 800 according to an embodiment of the present invention. The movable clip catheter management device 800 shows the connected catheter clip 310 connected to the exterior surface of the handle 420 by a hinge 810.

In one embodiment, the hinge 810 is a living hinge that allows the connected catheter clip 310 to move away from the exterior surface of handle 420. In this embodiment, the hinge 810 allows the distance "d" between the interior surface of clip 410 and the exterior surface of handle 420 to either increase or decrease to better accommodate the catheter shaft 150 that is looped about either side of the catheter clip 310.

In another embodiment, the hinge 810 is a non-living hinge of metal elasticity composed of a material such as nitinol or a steel spring. In this embodiment the hinge 810 allows the connected catheter clip 310 to bend closer or further away from the exterior surface of handle 420. The hinge 810 allows the catheter clip 310 to accommodate loops of the catheter shaft 150. As the catheter shaft 150 is looped through one side of the connected catheter clip 310, for the side receiving the loops of the catheter shaft 150, the distance "d" between the interior surface of clip 410 and the exterior surface of handle 420 increases to accommodate the loops of the catheter shaft 150. As a result, for the side of the connected catheter clip 310 not receiving the loops of the catheter shaft 150, the distance "d" between the interior surface of clip 410 and the exterior surface of handle 420 decreases.

The aforementioned embodiments of the hinge 810 can be incorporated into the catheter management clip 160 of FIG. 2 and FIG. 4. In another embodiment where the hinge 810 is incorporated into the catheter management clip 160 of FIG. 2 and FIG. 4, the handle body 180 has a recess that allows the catheter management clip 160 to be recessed into the handle body 180 when not in use.

Figure 9:
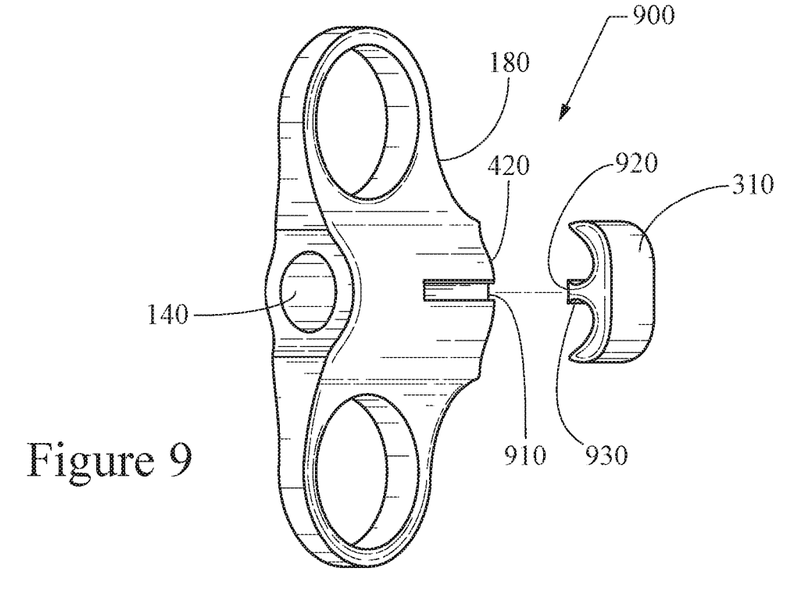
FIG. 9 illustrates an exploded view of the catheter management clip that is removable from the body of the handle according to an embodiment of the present invention.

FIG. 9 illustrates a removable clip catheter management device 900 according to an embodiment of the present invention. The removable clip catheter management device 900 shows the handle body 180 with a receptor 910 on the exterior surface of handle 420. The connected catheter clip 310 has a clip base 930 that interacts with the receptor 910 to secure the connected catheter clip 310 to the handle body 180.

In one embodiment, the receptor 910 is a recess in the handle body 180. The receptor 910 is partially below the exterior surface of handle 420. In this embodiment, the clip base 930 of the connected catheter clip 310 fits into the receptor 910 so that the base 920 of the connected catheter clip 310 is against the surface of the receptor 910. The connected catheter clip 310 can be attached to the exterior surface of handle 420 by sliding the connected catheter clip 310 in a direction that moves the connected catheter clip 310 closer to the opening for a slidably disposed stem 140. The connected catheter clip 310 can be removed from the exterior surface of handle 420 by sliding the connected catheter clip 310 in a direction that moves the connected catheter clip 310 away from the opening for a slidably disposed stem 140.

In another embodiment, the receptor 910 allows the connected catheter clip 310 to snap onto the handle body 180. In this embodiment, the connected catheter clip 310 does not dislodge easily, but can be removed from the handle body 180 with minimal force.

The aforementioned embodiments of the receptor 910 and the clip base 930 can be incorporated into the catheter management clip 160 of FIG. 2 and FIG. 4.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. A catheter management device comprising:
   a handle comprising a body, the body having a convex exterior portion;
   an elongate catheter shaft extending from the handle; and
   a curved clip, wherein said curved clip is located on the body of said handle, wherein said curved clip comprises a concaved interior portion that is spaced apart and opposite from the exterior portion of the body, wherein the interior portion of said curved clip and the exterior portion of said body have a distance between the two that decreases over the length of said curved clip towards a free end of said curved clip, and wherein the curved clip is configured to secure a portion of the catheter shaft between the interior portion of said curved clip and the exterior portion of said body.

2. The catheter management device as claimed in claim 1, wherein two curved clips are located on opposite sides of said handle and the openings of said two curved clips are curved in the same direction.

3. The catheter management device as claimed in claim 1, wherein two curved clips are located on the same side of said handle, and wherein portions of said two curved clips are connected together.

4. The catheter management device as claimed in claim 1, wherein the interior portion of said curved clip is lined with a material that is configured to provide friction with the catheter shaft.

5. The catheter management device as claimed in claim 1, wherein said curved clip is curved to form a funnel shaped opening between said interior portion of said curved clip and said exterior portion of said handle.

6. The catheter management device as claimed in claim 1, wherein said curved clip is attached to the body of said handle by a hinge.

7. The catheter management device as claimed in claim 6, wherein said body of said handle has a recess that said curved clip fits into.

8. The catheter management device as claimed in claim 1, wherein said curved clip is removably attached to said body of said handle.

9. The catheter management device as claimed in claim 8, wherein said curved clip is slidably attached to said body of said handle.

10. A method of catheter management, the method comprising the steps of:
    providing a handle having an elongate catheter shaft extending there from;
    providing a clip on said handle, wherein said clip contains a curved body having an interior surface that is spaced apart from and is opposite a rounded exterior surface of said handle, wherein the distance between the interior surface of said clip and the exterior surface of said handle decreases over the length of said clip towards a free end of said clip; and
    coiling the catheter shaft and inserting a portion of the catheter shaft between said interior surface of said curved body of said clip and said exterior surface of said handle, wherein said coiling of said length of said catheter is not limited by the direction of said coiling of said catheter.

11. A method of catheter management, as claimed in claim 10, wherein interior surface of said clip is lined with a material that provides friction.

12. A method of catheter management, as claimed in claim 10, wherein two curved clips are located on both sides of said handle and the openings of said two curved clips are curved in the same direction.

13. A method of catheter management, as claimed in claim 10, wherein two curved clips are located on the same side of said handle wherein portions of said two curved clips are connected.

14. A method of catheter management as claimed in claim 10, wherein said clip is attached to said handle by a hinge.

15. A method of catheter management as claimed in claim 10, wherein said clip is removably attached to said handle.

16. A method of catheter management as claimed in claim 10, wherein said handle has a recess that said clip fits into.

* * * * *